United States Patent [19]

Grasser

[11] Patent Number: 4,823,774

[45] Date of Patent: Apr. 25, 1989

[54] COMBINATION PATIENT SUPPORT TABLE AND SHOCK WAVE TUBE

[75] Inventor: Franz Grasser, Eggolsheim, Fed. Rep. of Germany

[73] Assignee: Siemens Aktiengesellschaft, Berlin and Munich, Fed. Rep. of Germany

[21] Appl. No.: 58,760

[22] Filed: Jun. 5, 1987

[30] Foreign Application Priority Data

Jul. 31, 1986 [DE] Fed. Rep. of Germany ... 8620535[U]

[51] Int. Cl.$^4$ .............................................. A61B 17/22
[52] U.S. Cl. .................................. 128/24 A; 128/328; 269/322
[58] Field of Search .................... 128/328, 24 A, 660; 378/20, 69, 195, 208, 209; 5/81 R, 81 B, 81 C; 269/322, 324

[56] References Cited

U.S. PATENT DOCUMENTS

| | | | |
|---|---|---|---|
| 3,810,263 | 5/1974 | Taylor .................................... | 5/81 R |
| 4,017,737 | 4/1977 | Hudson et al. ...................... | 378/208 |
| 4,099,059 | 7/1978 | Distler ................................. | 378/195 |
| 4,131,802 | 12/1978 | Braden et al. ....................... | 378/208 |
| 4,589,126 | 5/1986 | Augustsson et al. ................ | 378/209 |
| 4,610,249 | 9/1986 | Makofski et al. ................... | 128/328 |
| 4,615,042 | 9/1986 | Schmedemann ..................... | 378/209 |
| 4,681,098 | 7/1987 | Lee ................................. | 5/81 R X |

OTHER PUBLICATIONS

Siemens Prospekt "Lithostar".

*Primary Examiner*—Ruth S. Smith
*Attorney, Agent, or Firm*—Hill, Van Santen, Steadman & Simpson

[57] ABSTRACT

The invention is directed to a patient supporting table for an apparatus for the disintegration of calculi in the body of a patient including a bearing surface which has an opening in which a shock wave tube for generating shock waves serving for the disintegration of the calculi is arranged. In order to enable an exact positioning of the patient relative to the opening or, respectively, relative to the shock wave tube in a simple way, conveyors are provided by which the patient is displaceable on the bearing surface relative to the opening.

2 Claims, 1 Drawing Sheet

COMBINATION PATIENT SUPPORT TABLE AND SHOCK WAVE TUBE

BACKGROUND OF THE INVENTION

1. Field of the Invention

The invention is directed to a patent supporting table for an apparatus for the disintegration of calculi in the body of a patient, comprising a bearing surface that has an opening in which a shock wave tube for generating shock waves serving for the disintegration of the calculi is arranged.

2. Description of the Prior Art

Such a patient supporting table is disclosed in the prospectus of Siemens Ag, "Lithostar-Universeller Urologischer Arbeitzplatz fuer Therapie und Diagnostik", publication code: A91001-M1027-G490-01 PA 4864. For treating the patient, the shock wave tube situated in the opening and outputting focused shock waves is acoustically coupled such to the body surface or the patient lying on the bearing surface that the calculus to be disintegrated, for example a kidney stone, is situated in the focus of the shock waves. An exact positioning of the patent relative to the shock wave tube is required for this purpose. In the known patient supporting table, the bearing surface together with the patient lying thereon are therefore motor-displaceable relative to the shock wave tube in the longitudinal body direction of the patient and transversely relative thereto. In order to prevent the usually anesthetized patient from falling through an opening, however, this comprises only relatively small dimensions in the longitudinal body direction of the patient. Since, further, the shock wave tube is arranged in the opening of the bearing surface during the displacement of the bearing surface, the bearing surface can only be displaced by a small dimension relative to the shock wave tube in the longitudinal body direction of the patient since the limiting edges of the opening would otherwise strike the shock wave tube and move it from its predetermined position or even damage it. Given the known patient supporting table, therefore, the treating physicians and the assisting personnel must initially manually align the patient at least in his longitudinal body direction with such precision on the bearing surface that his exact positioning within the range of adjustment of the bearing surface limited by the dimensions of the shock wave tube and of the opening can ensue under motor drive. Due to the fact that the patient is anesthetized, this involves considerable physical exertions. Further, there is the risk that a patient who, for example, is already exactly positioned in transverse direction of the bearing surface will again be shifted. Further, this procedure is not particularly gentle on the patient since considerable forces must be exerted on the patient.

SUMMARY OF THE INVENTION

An object of the invention is to provide a patient supporting table of the type initially described such that an exact positioning of the patient relative to the shock wave tube is possible in a simple way without enlarging the opening, without this involving physical exertion for the treating physicians and the assisting personnel and without significant forces having to be exerted on the patient.

This object is achieved in accord with the invention in that conveying means are provided by means of which the patient is displaceable on the bearing surface relative to the opening. The patient who has at least a part of his body lying on the conveying means can thus be easily shifted relative to the opening and can be exactly positioned without this involving particular physical exertions for the treating physicians and for the assisting personnel. When the conveying means are motordriven, physical exertions are completely eliminated. The positioning procedure is also more gentle on the patient, since only slight forces are exerted on him. When, moreover, the conveying means comprise an unlimited displacement path, the patient can be placed on the bearing surface in a nearly arbitrary position, and can be subsequently unproblematically positioned relative to the opening with the conveying means.

German published application No. 26 19 468 in fact discloses a computer tomography comprising two beds whose bearing surface is respectively provided with conveyor means, whereby the beds are arranged such that their ends facing one another are arranged at a slight distance from one another so that a narrow gap is present for the passage of x-rays; however, the gap is only provided in order to avoid imagings of the beds by the x-radiation. No apparatus parts whatsoever, particularly no shock wave tubes, are arranged in the gap. In view of the slight width of the gap, they would likewise not find space therein. The gap of the known computer tomograph is thus not a matter of an opening in the sense of the present invention in which a part residing in engagement with the patient is arranged.

An especially simple execution of the patient supporting table of the invention is achieved when the bearing surface is formed by the conveying means. In accord with the modification of the invention, the conveying means can then be formed by at least one conveyor belt, whereby a good support of the patient and an unlimited displacement path of the conveying means are achieved in a simple way. Since the conveyor belt enables displacements of the patient in only one direction, for example in the longitudinal body direction of the patient, measures must be undertaken in order to be able to shift the body of the patient in the direction proceeding at a right angle thereto, this, for example, being capable of being achieved in that the bearing surface is displaceable overall in this direction under motor drive. It is thereby expedient to fashion the bearing surface motor-displaceable at a right angle relative to the longitudinal body direction of the patient, since the opening can then extend over the entire width of the bearing surface without the risk of the patient falling through, so that an adequately great displacement path is available in order to be able to exactly position the patient in this direction.

It is especially advantageous when the conveying means in accord with an embodiment of the invention are composed of two conveying paths arranged at both sides of the opening, the ends thereof facing one another limiting the opening. In this case, the patient has his body lying at both sides of the opening, lying on the conveying means forming the respective conveying path. Since these execute movements in the same direction when positioning the patient, no frictional forces between the body of the patient and the bearing surface can arise, these potentially opposing an easy displaceability and an exact positionability of the patient. Insofar as the conveying means are motor-driveable, it can already be sufficient when at least one conveying path is motor-driveable. If it is proved that both conveying paths are motor-driveable, it is expedient to motor-drive these synchronously and in the same direction for positioning the patient, since unnecessary stresses on the body but particularly on the skin of the patient are avoided. One embodiment of the invention provides that, in addition, both conveying paths are motor-driveable independently of one another. In that only one of the two conveying paths is motor-driven and the ohter is decellerated or in that body conveying paths are driven in opposite directions, namely, it is possible to stretch the skin of the patient situated in the region of the opening, this being required for an especially effective acoustical coupling of the shock wave tube to the body of the patient.

BRIEF DESCRIPTION OF THE DRAWINGS

An exemplary embodiment of the invention is shown in the attached drawing. Shown are.

DESCRIPTION OF THE PREFERRED EMBODIMENTS

Figure 1:
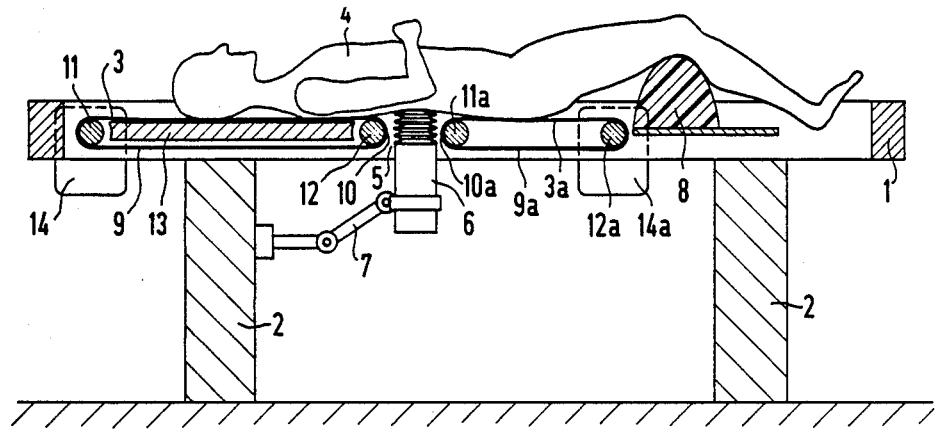
FIG. 1 is a longitudinal section along line I—I in FIG. 2 through a patient supporting table of the invention.
Figure 2:
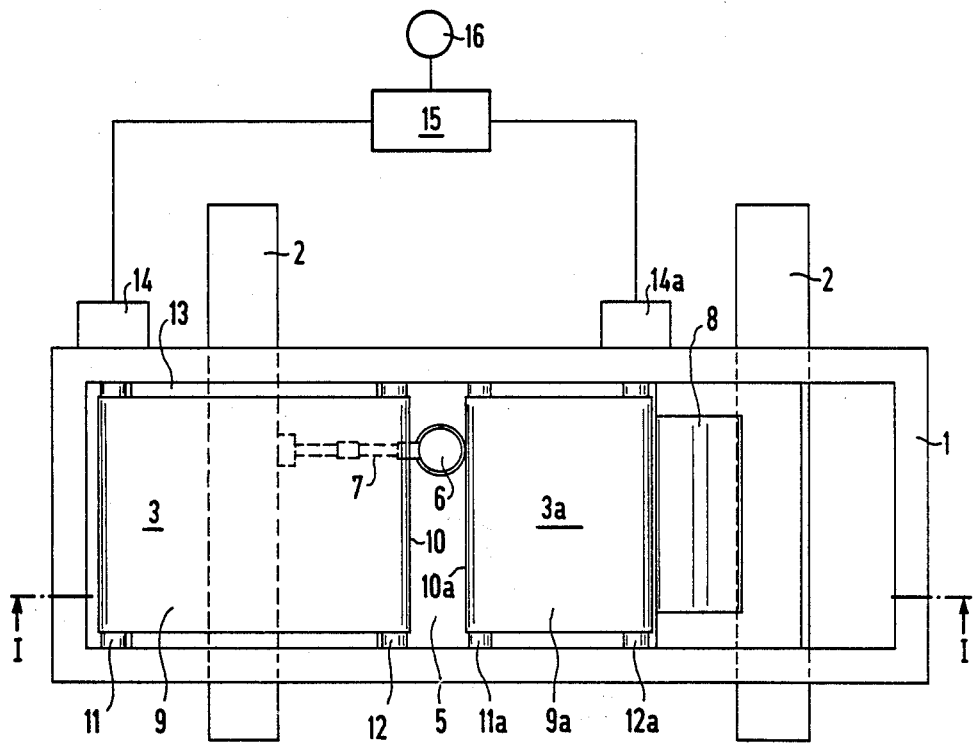
FIG. 2 is an elevation of the patient supporting table of the invention.

FIGS. 1 and 2 show a patient supporting table of the invention which is part of an apparatus for the disintegration of calculi in the body of a patient 4, having a frame 1 with stands 2 and having a bearing surface 3, 3a for a patient 4 who is not shown in FIG. 2 for reasons of clarity. The bearing surface 3, 3a includes an opening 5 through which a region of the body surface of the patient is accessible for treatment with a shock wave tube 6. This is secured to a stand 2 with a retaining arm 7. The shock wave tube 6 is acoustically coupled to the body of the patient 4 and emits focused shock waves which serve the purpose of disintegrating calculi situated in the body of the patient 4. To this end, the patient 4 whose legs are supported by a cushion 8 must be positioned such on the bearing surface 3, 3a relative to the opening 5 and relative to the shock wave tube 6 situated therein that the calculi to be disintegrated are situated in the focus of the shock waves.

The patient supporting table of the invention therefore comprises conveying means for shifting the patient 4 relative to the opening 5, these conveying means being composed of two conveying paths arranged at both sides of the opening 5 whose ends 10, 10a facing one another limit the opening 5. The conveying paths are fashioned as conveyor belts 9, 9a which proceed over rollers 11, 12, and 11a, 12a seated rotatably in the frame 1, proceeding in longitudinal body direction of the patient 4 and, thus, allowing a positioning of the patient 4 relative to the opening 5 in this direction. The ends 10 and 10a of the conveying paths limiting the opening 5 are formed by the rollers 12 and 11a and by the conveyor belts 9 and 9a running thereover. Displacements of the patient 4 relative to the shock wave tube 7 transversely relative to the longitudinal body of the direction of the patient 4 are possible in that the frame 1 together with the bearing surface 3, 3a is attached to the stands 2 in motor-displaceable fashion (not shown).

The bearing surface 3, 3a is formed directly by the conveyor belts 9, 9a. In addition to being supported by the conveyor belt 9 in the region of his upper body, the patient 4 is also supported by a plate 13 provided between the sides of the conveyor belt 9, whereas he is carried only by the conveyor belt 9a in the region of his lower body.

The conveyor belts 9 and 9a can be motor driven by motors 14, 14a which are coupled to the rollers 11 and 12a. To this end, as may be seen from FIG. 2, they are connected to a current source 16 via a control means 15. The control means 15 is fashioned such that only the conveyor belt 9 or 9a is optionally drivable by means of the respectively allocated motor 14 or 14a. Further, the control means 15 allows both conveyor belts 9, 9a to be driven synchronously and in the same direction with the motors 14, 14a.

In the exemplary embodiment which has been set forth, the conveying means are fashioned as conveyor belts. However, it is also possible to fashion the conveying means with a plurality of rollers, balls or the like.

Given a suitable arrangement and formation of the conveying means, moreover, the body of the patient can also be shifted transversely relative to the longitudinal axis this body or can be shifted in arbitrary directions relative to the opening, in contrast to the illustrated exemplary embodiment.

In the case of the described exemplary embodiment, the patient supporting table of the invention is used when disintegrating calculi situated in the body of a patient, however, it can be employed for all diagnosis and therapy procedures wherein a region of the body surface of the patient must be accessible through an opening in the bearing surface and wherein a displaceability of the patient relative to the opening is required.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A patient support table in combination with a shock wave tube for generating shock waves serving for disintegrating calculi in the body of a patient, said table including a bearing surface having an opening in which the shock wave tube is arranged, the improvement comprising conveying means in the form of conveyor belts arranged at both sides of the opening whose ends facing one another limit the opening, by means of which the patient is displaceable on the bearing surface relative to the opening, a drive motor for each conveyor belt and a control means for the drive motors being provided for selectively driving the conveyor belts synchronously and in the same direction and for driving the conveyor belts independently of the movement of one another.

2. A patient support table in combination with a shock wave tube for generating shock waves serving for disintegrating calculi in the body of a patient, said table including a bearing surface having an opening in which the shock wave tube is arranged, the improvement comprising conveying means in the form of conveyor belts arranged at both sides of the opening whose ends facing one another limit the opening, by means of which the patient is displaceable on the bearing surface relative to the opening, a drive motor for each conveyor belt and a control means for the drive motors being provided for selectively driving the conveyor belts synchronously in the same direction, for driving the conveyor belts in opposite directions from one another and for driving the conveyor belts independently of the movement of one another.

* * * * *